US007042567B2

(12) United States Patent
Balas et al.

(10) Patent No.: US 7,042,567 B2
(45) Date of Patent: May 9, 2006

(54) IMAGING METHOD AND APPARATUS FOR THE NON-DESTRUCTIVE ANALYSIS OF PAINTINGS AND MONUMENTS

(75) Inventors: Konstantinos Balas, Heraklion (GR); Demetrios Pelecoudas, Patras (GR)

(73) Assignee: Foundation of Research and Technology, Crete (GR)

( * ) Notice: Subject to any disclaimer, the term of this patent is extended or adjusted under 35 U.S.C. 154(b) by 366 days.

(21) Appl. No.: 10/203,587

(22) PCT Filed: Dec. 8, 2000

(86) PCT No.: PCT/GR00/00039

§ 371 (c)(1),
(2), (4) Date: Oct. 30, 2002

(87) PCT Pub. No.: WO02/46710

PCT Pub. Date: Jun. 13, 2002

(65) Prior Publication Data

US 2003/0117620 A1 Jun. 26, 2003

(51) Int. Cl.
*G01J 3/28* (2006.01)
(52) U.S. Cl. .................. 356/326; 356/332
(58) Field of Classification Search .......... 356/326, 356/328, 329, 332; 382/165, 181, 329; 250/459.1
See application file for complete search history.

(56) References Cited

U.S. PATENT DOCUMENTS 5,461,475 A * 10/1995 Lerner et al. ............... 356/300
5,479,258 A * 12/1995 Hinnrichs et al. .......... 356/326
5,485,530 A * 1/1996 Lakowicz et al. .......... 382/191
5,491,344 A * 2/1996 Kenny et al. ............. 250/461.1
5,737,076 A * 4/1998 Glaus et al. ................ 356/310
6,069,696 A * 5/2000 McQueen et al. .......... 356/326
6,111,640 A * 8/2000 Hedman et al. ............ 356/300
6,135,965 A * 10/2000 Turner et al. ............... 600/476
6,373,568 B1 * 4/2002 Miller et al. ................ 356/326
6,703,621 B1 * 3/2004 Wolleschensky .......... 250/459.1

FOREIGN PATENT DOCUMENTS

WO WO 99/02950 * 1/1999

OTHER PUBLICATIONS

Shimoyama et al, Non-destructive Analysis of Ukio-e Prints, 1996, Textile Research Associates, York, Dyes in History and Archaeology, No. 15.*

Anglos et al, Laser Spectroscopic and Optical Imaging Techniques in Chemical and Structural Diagnostics of Painted Artwork, Oct. 1999, American Laboratory, vol. 31, No. 20.*

* cited by examiner

*Primary Examiner*—Layla G. Lauchman
(74) *Attorney, Agent, or Firm*—Herbert Dubno

(57) ABSTRACT

This invention refers to an imaging method and apparatus capable of performing non-destructive, in situ analysis of art-objects. The invention relays on the comparison of diffuse reflectance and/or fluorescence spectra (intensity vs. wavelength), of painting material models of known composition, with the intensities emitted and captured at the same wavelengths and for any spatial point of the art-object of unknown composition. This composition, performed for any spatial point of the area of interest, improves notably the diagnostic information and enables the analysis of heterogeneous art-objects.

15 Claims, 2 Drawing Sheets

IMAGING METHOD AND APPARATUS FOR THE NON-DESTRUCTIVE ANALYSIS OF PAINTINGS AND MONUMENTS

CROSS REFERENCE TO RELATED APPLICATION

This application is a national stage of PCT/GR00/00039 filed 8 Dec. 2000.

FIELD OF THE INVENTION

The present invention relates to an imaging method and apparatus for the nondestructive analysis of paintings and monuments.

BACKGROUND OF THE INVENTION

Technical analysis of paintings is intended to detect retouching, pentimenti, underdrawings and to identify original and added material (e.g. pigments, binding media, coatings, retouching). This information is essential for dating and authentication of the artwork and contributes significantly to our understanding of art objects. In addition, it facilitates the evaluation of the physical condition (deterioration, interventions) and directs conservation decisions.

Traditionally, the analysis of paintings has been restricted to invasive investigations and is carried out ex situ. This approach has the drawback of being harmful to the painting—as it requires samples to be taken—and provides only spot specific information that is not necessarily representative of the object in its context. Consequently the development of non-invasive techniques that can be used in situ and provide global information will enjoy a great impact.

Over the last two decades there have been substantial advances made in the application of modern scientific techniques to the chemical and structural analysis of works of art. However there is still room for improvement as the analysis of artworks is generally a very complex and demanding problem. A very important issue in this respect is the development and use of non-destructive analytical techniques, which can be applied in situ. In response to the demand for non-destructive analytical devices in the art conservation field, a variety of imaging and spectroscopic techniques have been developed and used for the in situ examination of artwork materials.

Film photography has been extensively used to capture artwork images in the visible, near ultraviolet (NUV) and near infrared (NIR) parts of the spectrum. A variety of different imaging devices have also been used, ranging from film to analog (video) and digital cameras. Moreover, different cameras with spectral sensitivities restricted either to the visible or to the near infrared (NIR) part of the spectrum have been used in order to obtain diagnostic information for the artwork under analysis. In particular, imaging in the near infrared enables the visualization of underdrawings, relying on the phenomenon that in general the overlying pigments become transparent in this wavelength range. Broadband fluorescence photography provides information for the condition of coatings (such as varnishes) and enables the localization of previous restoration interventions. A variety of light dispersion spectroscopic techniques have also been used in situ and ex situ for the identification of painting materials. Materials with the same color appearance, determined by the similar diffuse reflectance spectra in the visible, may have different spectral patterns outside the visible part of the spectrum. Compositional alterations associated with the material deterioration can be recorded by measuring absorption, fluorescence, or (elastic, non-elastic) scattering signals, providing quantitative diagnostic information. Fluorescence and diffuse reflectance spectra are in general broad in the visible and the NIR part of the spectrum due to the complicated nature of the artwork material and due to light-material interaction mechanisms that are involved in these phenomena. Owing to this fact, these spectroscopic techniques are suitable for detecting in situ chemical and structural alterations and for the differentiation of pigments with the same color appearance but different chemical composition. Raman and FTIR spectroscopy provide improved, molecular-specific diagnostic information, since the acquired spectra contain fingerprint information for a specific point area of the artwork material under analysis. Until now the use of these techniques have been restricted to the experimental-ex situ analysis of material samples, mainly due to the required complicated instrumentation. Laser Induced Breakdown Spectroscopy LIBS) is a novel promising technique for in situ analysis, it requires however laser ablation of a spot area and the subsequent spectroscopic analysis of the created plume. For this reason this technique is considered as minimally invasive and in several cases (e.g. fragile and thin material) it is not applicable. Apart from the above mentioned, the common problem that restricts seriously the applicability of conventional spectroscopic methods to the in situ analysis of artwork is that they provide point information, which is inadequate in cases where complicated materials, characterized by a high spatial variability of their contextual features are examined. Moreover the point area under analysis has to be determined by the user, which in several cases is not capable of detecting and focussing his attention in artwork areas that are subjected to alterations. This results in a reduction of the accuracy of these methods due to probing errors.

Summarizing the above mentioned, conventional spectrometers provide a large amount of spectroscopic (analytical) information about one localized site of the object, whereas conventional broadband imaging provides a modest amount of spectral information (resolution), but for a significant area of the object.

In the field of art conservation, there are applications reported where cameras sensitive in the visible and in the NIR are filtered with optical filters, thus enabling the selection of the imaging center wavelength with the aid of a filter tuning mechanism. In the visible part of the spectrum these cameras are used for accurate color reproduction, while in the NIR part of the spectrum filter tuning enables the determination of the appropriate imaging band, at which the maximum imaging information for the underlying features is obtained. Based on the above mentioned it reasonable to suggest that the combination of the advantages of both imaging and spectroscopy will constitute a significant step forward in non destructive analysis and documentation of art-objects and monuments. Although Raman, FTIR and LIBS spectroscopies provide improved analytical information it is very difficult, or in the LIBS case impossible, to operate in imaging mode. In contrast, there is not any fundamental or technological restriction for the development of imaging systems capable of capturing diffuse reflectance and/or fluorescence spectroscopic information for the entire surface under examination. Of course, as mentioned above, these techniques suffer from the main drawback that the captured spectra contain pure information or painting material identification.

OBJECT OF THE INVENTION

The object of this invention is to provide an imaging method and apparatus capable of performing non-destructive, in situ analysis of art-objects.

SUMMARY OF THE INVENTION

The method relies on the comparison of diffuse reflectance and/or fluorescence spectra (intensity vs. wavelength), of painting material models of known composition, with the intensities emitted and captured at the same wavelengths and for any spatial point of the art-object of unknown composition. This comparison, performed for any spatial point of the area of interest, improves notably the diagnostic information and enables the analysis of heterogeneous art-objects. The present invention thus refers to an imaging method and apparatus for the non-destructive technical analysis of artistic and/or historic value (paintings, monuments etc) of unknown structure and composition hereunder described with the term "object".

Key points are:

Determination of the diffuse reflectance and/or of the fluorescence spectral differences of all the possible groups of object material samples that demonstrate the same or of similar color characteristics but of different chemical composition. Spectra are captured and analyzed in a wide spectral range and for a variety of light excitation and response capturing wavelengths.

Determination of the optimum excitation-capturing spectral band combinations for the differentiation between groups of object material samples with the same or similar color characteristics. Imaging of the area of interest of the original object under analysis at the predetermined optimum combinations of excitation—image capturing wavelength band(s), for the specific material group under consideration. From these data, the spectral distribution of the light intensities, expressed by the object, can be calculated as a function of spatial location, which subsequently can be compared with the captured spectra of the object material models. Although the original materials under analysis are typically complicated and heterogeneous, this comparison can provide valuable information for the in situ, non-destructive identification and mapping of original materials of unknown structural and compositional characteristics. This is supported by the fact that in each historical period, the artists used a few different painting materials i.e. 5 reds or 10 greens of different chemical composition, which can in general differentiated and identified by comparing reflectance and fluorescence spectral data.

SPECIFIC DESCRIPTION

Figure 1:
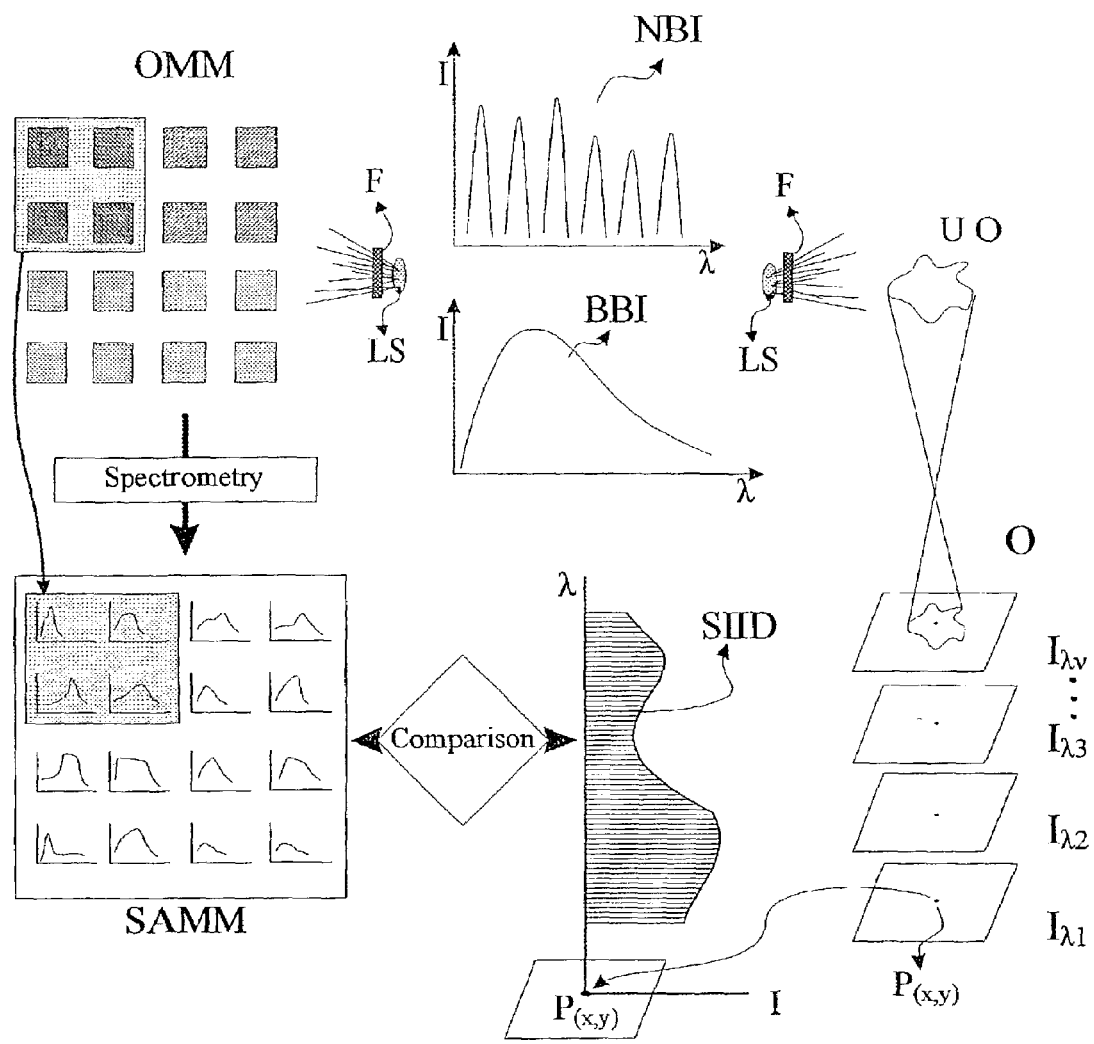
FIG. 1 is a diagram illustrating the principles of the invention.

FIG. 1 illustrates graphically the basic concept of the method. The light source (LS) emits photons with energies ranging from ultraviolet to infrared. The light source (LS) is used to illuminate either the original object of artistic and/or historic value (paintings, monuments etc) of unknown structure and composition (UO) or object material models (replicas) of known structure and composition (OMM). Narrow band illumination (NBI) of both original object and object material models can be obtained with the aid of a variety of methods including lasers, single or arrays of light emission diodes (LEDs). It can also be obtained by filtering a broad band light source (LS) with a single optical filter with a plurality of optical filters that transmit different spectral bands (F). In case of multiple filters, the illumination wavelength band can be tuned with the aid of a filter interchanging mechanism.

A variety of object material models (OMM) can be constructed following the techniques used from the artists in each historical period. These models include pure painting materials as well as combinations of pigments, binding media, coatings etc.

Object material models (OMM) are excited with a broad band or a narrow band light source and their response to the incident light is recorded in a wide spectral range from ultraviolet to near infrared. Measurements are performed after appropriate calibration against standard samples. The measured data can be classified according several criteria such us material coloring, historic period, artist's style, etc. For each particular group of (OMM) with the same color appearance but with different chemical composition, optimum material illumination and response wavelength band(s) are determined at which the maximum spectral differentiation is obtained. In order to improve the optical information for the differentiation, ratios of intensities captured at different wavelengths are also considered and compared.

The original object of unknown composition (UO) can also be optically excited with any of the above mentioned illumination modes, broad band (BBI) or narrow band (NBI) and the object's response to this excitation is recorded with the aid of a two-dimensional optical detector. Single broad and narrow band image of a plurality of narrow band images can be captured at different wavelength bands simultaneously or in a time succession and for a wide spectral band ranging from ultraviolet to the mid-infrared.

During the examination of an original object of unknown compositional and structural characteristics, the area of interest is optically excited and its response (diffuse reflectance and/or fluorescence) is captured at spectral bands at which maximum diagnostic information is obtained for the identification of the materials used to develop this area. The selection of optimum imaging bands, conditions and modes (diffuse reflectance, fluorescence) is based on the spectral information captured from object material models with the same color characteristics with the area under analysis. The intensities of image points with the same spatial registration $P(x,y)$ versus the image capturing wavelengths $I\lambda_1$, $I\lambda_2$, $I\lambda_3$ ... $I\lambda_y$, form the spectral image intensity distribution (SIID) for the point $P(x,y)$. The (SIID) can be calculated for any spatial point or group of points. This distribution could be a full spectrum depending on the spectral resolution of the image capturing and acquisition apparatus employed.

Comparison of (SIID) with the spectra that correspond to the object material models (SAMM) with similar macroscopic and other characteristics, including color historical data, construction techniques etc. enable the identification of the unknown material at any spatial location of the examined area.

Figure 2:
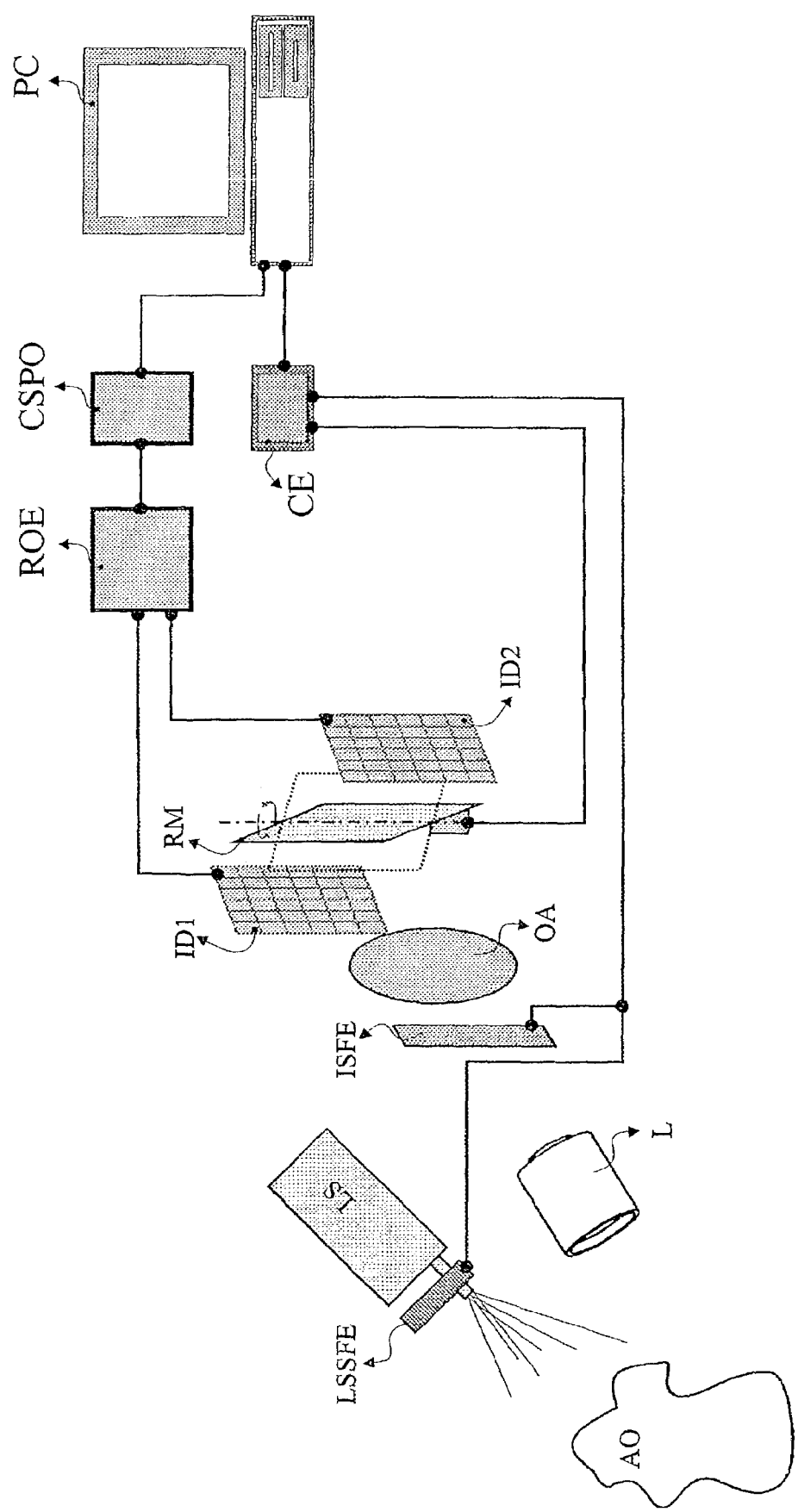
FIG. 2 is a diagram of the apparatus.

FIG. 2 illustrates a block diagram of the imaging apparatus for the non-destructive analysis of paintings and monuments. The art object (AO) is illuminated by a light source (LS) which emits photons with wavelengths ranging from ultraviolet through infrared. When narrow band illumination is required, the emitted light passes through light source spectral filtering element(s) (LSSFE), which enables the selection and the tune of the of the center wavelength. The light re-emitted by the object is collected by a lens (L) or a microscope, passes through the imaging spectral filtering elements (ISFE) and the optical aperture (OA) and the formed image of the object is recorded by one or more imaging detectors (ID1), (ID2). The light source spectral filtering element(s) (LSSFE) and the imaging spectral filtering elements (ISFE) may comprise a rotating band pass filter wheel, which enables the selection of the illumination and/or the imaging center wavelength. The rotation of the filter wheel and therefore the selection of the illumination and/or the imaging center wavelength can be controlled with the aid of controlling electronics (CE). The apparatus embodies more than one interchangeable optical detectors (ID1), (ID2) with different spectral sensitivities in cases that extended spectral sensitivity is required. This extension enables the direct comparative imaging of the object in a wide spectral range such as from 200 nm through 2500 nm, something untenable with a single detector. Imaging in a wide spectral range and trough the same optical aperture is very informative since it enables the selective imaging of the various layers of the object and the determination of spectral bands at which object materials with the same color appearance are differentiated. The optical detectors can be interchanged behind the optical aperture (OA) with the aid of sliding mechanism, on which the detectors have been affixed. Another method employs a rotating mirror (RM), which deflects the optical rays and direct them onto the one or the other detector. The rotation of the mirror or the linear movement of the detectors can also be controlled with the aid of controlling electronics. The recorded by the detectors images are converted to electrical signals, which are transferred with the aid of read-out electronics (ROE) and amplified, modulated and digitized with the aid of the camera signal processing unit (CSPO). Both camera signal processing unit (CSPO) and controlling electronics (CE) can be interfaced with a personal computer (PC). The embodied to the apparatus hardware and software enables the selection of the imaging mode and the image calibration, capturing, acquisition processing and analysis. With the aid of software means, the stored diffuse reflectance and/or fluorescence images of the area under analysis can be automatically compared with the previously stored spectral data of the object material models, thus facilitating the non-destructive identification of the unknown materials of the object.

The invention claimed is:

1. A method of nondestructive analysis of an object selected from the group which consists of paintings and monuments, comprising the steps of:
    (a) exposing the object to a polychromatic incident light beam including wavelengths ranging from ultraviolet to mid-infrared parts of the spectrum;
    (b) generating a broad-band image of the object in response to the incident light beam with wavelengths lying within spectral sensitivity limits of ultraviolet, visible, near-infrared and mid-infrared detectors and imaging photon energy converters used for image capture;
    (c) generating a plurality of narrow-band images corresponding to the broad-band image and comprised of the intensities of said broad-band image captured in respective narrow wavelength bands shorter than sensitivity spectral ranges of respective detectors;
    (d) for a multiplicity of object material models, obtaining light intensities under the same illumination and imaging conditions as used for the object at the same narrow wavelength bands; and
    (e) comparing for any spatial location of an examined area of the object onto which said incident light beam is directed, light intensities expressed by the materials constituting the object in said narrow wavelength bands with the light intensities expressed by the object material models in the same narrow wavelength bands under the same illumination and imaging conditions to determine and map the compositional characteristics of the material used to create the object.

2. The method defined in claim 1 wherein said object is exposed in step (a) to a plurality of illuminating light beams of different center wavelengths in time succession and wherein, in step (c) a plurality of narrow-band images are generated of the same or longer center wavelength as said illuminating light beams.

3. The method defined in claim 1 wherein the object is a painting and step (c) comprises tuning a center wavelength of a captured narrow-band image across the optical spectrum from the ultraviolet to the near-infrared in time succession to generate the narrow-band images and enable selective imaging, comparison, and compositional and structural analysis in succession of different layers of the painting from a surface to a backing thereof.

4. The method defined in claim 1 wherein the object material models and said narrow-band images are both reflectance and/or fluorescence images of at least a generally similar color appearance but different compositional characteristics enabling a direct comparison of the intensities expressed from the object and model materials and identification of the object material.

5. The method defined in claim 1 wherein spatial and spectral distribution of reflectance and/or fluorescence intensities derived from the captured narrow band images of the object area under analysis, are compared, in one or more spatial locations of the area under analysis, with the previously measured reflectance and/or fluorescence spectra of appropriate object material models, thus assisting the identification of the object material under analysis.

6. The method defined in claim 1, further comprising the step of ablating by laser an unwanted surface material from the surface of said object utilizing said images for control of the laser ablation.

7. The method defined in claim 1, further comprising the step of removing unwanted surface material from said object by chemical or mechanical action with on-line or off-line control of the removal in response to said images.

8. The method defined in claim 1 wherein, in step (a) the object is exposed to a blue-ultraviolet light beam and wherein in step (b) images comprising blue-ultraviolet reflecting images and/or visible-near infrared fluorescence images of the object are produced.

9. The method defined in claim 1 wherein, in step (e) surface features including texture, deposited material, varnishes and coatings are identified and high-lighted.

10. An apparatus for the nondestructive analysis of an object selected from the group which consists of paintings and monuments, comprising:
    a light source for exposing the object to a polychromatic incident light beam including wavelengths ranging from ultraviolet to mid-infrared parts of the spectrum;
    an optical detector for collecting light expressed by an examined area of the object exposed to the incident light beam for forming at least one image of said area; and
    for recording light intensity of the light expressed by said object as a function of location thereon;

control means for selecting center wavelengths of the incident light beam and images from said object and for controlling wavelengths and intensities of said incident light beam and image calibration and acquisition parameters;

an image display and image storage device connected to said optical detector; and a software-operated unit for operating said control means for controlling imaging wavelength, operating characteristics of said detector, said calibration, and imaging data analysis and processing, said detector being constructed and arranged to capture a plurality of reflectance and/or fluorescence images in various spectral bands to provide compositional and structural information assisting determination of conservation needs of the object and for on-line and off-line evaluation and control of restoration tasks.

11. The apparatus defined in claim 10 wherein said detector comprises a plurality of optical detectors with different spectral sensitivity and radiating deflection mechanisms for causing rays from said object onto said optical detectors upon passing through an optical aperture.

12. The apparatus defined in claim 10 wherein said detector comprises a CCD or a C-MOS 2 dimensional optical sensor optically coupled with infrared or ultraviolet-to-visible imaging converters.

13. The apparatus defined in claim 10 wherein said light source includes a plurality of light-emitting diodes with spectral emissions in wavelengths ranging from ultraviolet to mid-infrared parts of the spectrum.

14. The apparatus defined in claim 10 wherein said software-operated unit includes an oral network with algorithms and expert system for automated comparison of optical and other characteristics including historical and technical data as to said object with data as to object material models enabling nondestructive analysis of the object.

15. The apparatus defined in claim 10 wherein said light source, said detector, said image display device and said optical detector are integrated in a head-mounted platform.

* * * * *